United States Patent [19]

Slezak et al.

[11] Patent Number: 6,074,834

[45] Date of Patent: Jun. 13, 2000

[54] METHOD AND REAGENTS FOR ASSESSING LIPOPROTEIN METABOLISM

[75] Inventors: Sue Ellen Slezak, Downingtown; John H. Abel, Bethlehem; Barbara Obrepalska-Bielska, Bethlehem; Eugene A. Nau, Bethlehem; Kathy L. Gottlund, Kutztown, all of Pa.

[73] Assignee: Lehigh University, Bethlehem, Pa.

[21] Appl. No.: 09/036,454

[22] Filed: Mar. 6, 1998

Related U.S. Application Data

[60] Continuation of application No. 08/425,144, Apr. 19, 1995, abandoned, which is a division of application No. 08/004,848, Jan. 19, 1993, abandoned.

[51] Int. Cl.⁷ .................................................. G01N 33/567
[52] U.S. Cl. ..................... 435/7.1; 435/7.2; 435/7.4; 435/7.24; 435/7.5; 435/7.6; 435/7.8; 435/810; 424/450
[58] Field of Search ............................. 424/450; 435/7.1, 435/7.2, 7.4, 7.24, 7.5, 7.6, 7.8, 810

[56] References Cited

U.S. PATENT DOCUMENTS 5,135,848   8/1992   Abel et al. ............................. 435/7.21

*Primary Examiner*—Bennett Celsa
*Attorney, Agent, or Firm*—Michael R. Novack; John W. Fitzpatrick

[57] ABSTRACT

The present invention provides methods and reagents for assessing lipoprotein metabolism. The methods provided are applicable for use on multiple samples in a clinical laboratory, thus obviating the need for sophisticated instrumentation, such as flow cytometry. Selected cell types in a test sample are uniformly labelled with a detectable reporter substance, so that they may later be enumerated. Pre-determined lipoprotein receptors associated with the cells of interest are labelled with a receptor-selective marker, thereby to determine the number of lipoprotein receptors per cell in the test sample. Selected cells of interest are conveniently separated from the test sample by binding thereto a specific binding substance attached to a solid support. The specific binding substance binds specifically with a characteristic determinant of the cell subset of interest. The remainder of the test sample may be washed away or discarded. The separated cells of interest may then be enumerated by measuring the amount of detectable label associated therewith, hence to determine the number of lipoprotein receptors per cell in each test sample.

15 Claims, No Drawings

METHOD AND REAGENTS FOR ASSESSING LIPOPROTEIN METABOLISM

This application is a continuation of Ser. No. 08/425,144 filed Apr. 19, 1995 (abandoned), which is a Divisional application of Ser. No. 08/004,848 filed Jan. 19, 1993 (abandoned).

FIELD OF THE INVENTION

The present invention relates to biological testing and in particular to methods for identifying several classes of genetic defects that contribute to hypercholesterolemic conditions, and to reagents and test kits for performing such methods.

BACKGROUND OF THE INVENTION

Genetic hypercholesterolemia, which predisposes an individual to atherosclerosis, is a condition characterized by an abnormally elevated serum cholesterol level, wherein excessive dietary intake is not the sole cause of the elevation. Instead, the condition is caused by single or multiple autosomal mutations which affect either (i) the expression of lipoprotein receptors on the cell surface, or (ii) the capability of surface receptors to bind the apoprotein component of various lipoprotein particles. The nature of the mutation influences the patient's predisposition to respond to various classes of lipoprotein-lowering drugs. Such patients are currently identifiable by a failure to respond to diet therapy and by the commonality of certain abnormal characteristics among family members. Insofar as is known, no direct clinical diagnostic is currently available to positively identify the condition. Because of the need for this type of clinical information, several research tests have been used to elucidate the physiological mechanisms underlying the hypercholesterolemic patient's condition.

Research has focused on the identification of abnormal lipoprotein receptors, and has been concerned primarily with low density lipoprotein (LDL) receptors, which are thought to be most important in the predisposition for atherosclerosis. These methods have relied on genetic analysis of cells, comparing symptomatic and asymptomatic individuals. The receptor-coding DNA is subjected to restriction fragmentation and analysis, to identify genetic polymorphisms relating to abnormalities in lipoprotein receptors. See Japanese Patent Application No. 2291300 to Seiyaku (1990); PCT Application No. WO 88/03175 to Frossard (1988). Although genetic polymorphism analysis provides detailed information concerning genetic abnormalities which may be present, several points should be considered. First, not all genetic mutations manifest themselves as an impairment of the functioning of lipoprotein receptors or as an abnormality of the apoprotein region of the lipoprotein particle. Some mutations may be "quiet" mutations, whereby a nucleotide or amino acid substitution has no effect on the functionality of the resultant gene product. Secondly, although genetic techniques prove useful in the research laboratory, they are not generally applicable to use in the clinical laboratory because of the technical degree of difficulty and the sophistication of equipment that is required. Moreover, some mutations cannot be recognized through restriction enzyme analysis.

Alternative techniques have focused on assessing the functional aspect of the lipoprotein receptors, particularly LDL receptors. Radioactively labelled LDL particles (e.g., $^{125}$I-labelled protein components of the LDL particle) or LDL particles into which a fluorescent marker had been incorporated, have been utilized to determine differences between the number of LDL receptors on fibroblasts of genetically normal and abnormal individuals. Goldstein et al., J. Biol. Chem., 258: 4526–33 (1974). Polyclonal and monoclonal antibody methods have also been developed for the assessment of LDL receptor activity. Beisirgel et al., J. Biol. Chem., 257: 11923–31 (1981). Such antibodies have been utilized on whole cells using fluorescence or enzyme signal detection methods, and have also been applied to immunoblot analysis of various tissue extracts. Beisirgel et al., J. Biol. Chem., 257: 13150–56 (1982).

Lymphocytes from peripheral blood have been used to study the LDL receptor status in patients. Most of these studies have been disappointing due to the high uptake of LDL by peripheral blood monocytes in uninduced mononuclear samples, combined with the low receptor activity of lymphocytes due to receptor suppression by native serum lipoproteins. Ho et al., J. Clin. Invest., 58: 1465–74 (1976). Incubation for periods of 36 hours or more have greatly enhanced the receptor expression of these cells.

Although both radioactive methods and fluorescent methods can be used for determinations of LDL receptors on cell surfaces, fluorescent methods provide distinct advantages for clinical laboratory settings. Fluorescently labelled lipoprotein, detectable by flow cytometry and fluorometry, have been disclosed. In particular, the fluorescent compound 1,1'-dioctadecyl-2,2,2',2'-tetramethylindocarbocyanine perchlorate (DiI)-labelled human LDL particles have been used to measure surface binding and internalization into isolated lymphocytes at 37° C. The fluorometric methods were reported as being more signal-sensitive, but problematic since non-specific monocyte signals could not be eliminated from the analysis. Although less signal-sensitive, flow cytometric methods provided the advantage of being able to utilize light-scattering properties of the various cell subsets (e.g., monocytes, lymphocytes and neutrophils) to exclude the undesired monocyte and neutrophil populations from the analysis. Wojciechowski et al., Biochem. Soc. Trans., 15: 251–52 (1987). Further developments in this area have involved utilizing fluorescent labelled porcine LDL having a reportedly higher affinity for human LDL receptors than the previously-used human LDL, combined with methods to overcome the problem of repression of LDL receptors in fresh lymphocyte samples, as well as methods to evaluate receptor metabolism. These methodologies have also employed flow cytometry as the detection system. See, e.g., WO 91/06011 to Abel et al. (1991).

Clinical application of fluorescent techniques requiring flow cytometry for detection is problematic because of the low sensitivity as well as the inherent difficulties associated with flow cytometric analysis. Flow cytometry has become widely used in the clinical laboratory in analysis of white blood cell subsets, using monoclonal antibodies. But even under the standard protocols developed for such analyses, great inconsistencies can arise in test results due to the subjectivity of the analysis using flow cytometric methods. LDL receptor analysis histograms generated by flow cytometry are generally even more subjective. This combination of difficult analysis and expensive and technically demanding instrumentation renders clinical implementation of flow cytometry for LDL receptor analysis undesirable, if not completely unpracticable due to the high-volume multiple sample testing which would be required. Thus, there is considerable need for a clinically applicable method of identifying and analyzing potentially abnormal lipoprotein metabolism in a patient suspected of having genetically based hypercholesterolemia.

SUMMARY OF THE INVENTION

In accordance with the present invention, clinically applicable methods are provided for identifying and analyzing potentially abnormal lipoprotein metabolism in a patient. These methods can be practiced in batch mode, on multiple samples, using simple protocols and inexpensive instrumentation. It will be appreciated that the methods described hereinbelow may be utilized to assay the binding and internalization capability of any cell surface receptor. However, the invention will be described with specific reference to lipoprotein receptor determination. Exemplification on the basis of lipoprotein receptors should not be considered to limit the invention in any way.

According to one aspect of the invention, a method is provided for determining the relative number per cell of a pre-determined receptor (e.g., lipoprotein receptor) associated with a cell subset of interest in a test sample containing a mixed cell population, the subset of interest having at least one characteristic determinant. In a preferred embodiment, the test sample consists of a sample of whole blood from a patient, and the cell subsets of interest are lymphocyte populations.

According to the method, the cells comprising the subset of interest are uniformly labelled with a detectable reporter substance. The test sample comprising the cells is also contacted with a receptor-selective marker, which binds specifically to the pre-determined lipoprotein receptor, thus rendering the receptor detectable. Thus, the cell subset of interest contains two detectable labels: (1) a uniform label which can be used to quantitate the number of cells of interest in the test sample; (2) a receptor-selective label, which is used to quantitate the number of pre-determined lipoprotein receptors in the test sample. The test sample is then contacted with a specific binding substance which binds specifically to at least one characteristic determinant of the cell subset of interest, thereby forming a complex between the cell subset of interest and the specific binding substance. The complex comprising the specific binding substance and the cell subset of interest is separable from the other components of the test sample. In a preferred embodiment, the specific binding substance is affixed to a solid phase, such as a magnetic bead, so that the complex may easily be separated from other components of the test sample (e.g., by magnetic separation).

After the cell subset of interest is separated from the other components of the test sample, the amount of detectable reporter substance and the amount of receptor-selective marker are detected. A ratio of the amount of receptor-selective marker to the amount of detectable reporter substance is established to determine the relative number of lipoprotein receptors per cell in the cell subset of interest.

According to another aspect of the invention, the above-described method may be used to assess the functional metabolic capacity of a pre-determined lipoprotein receptor associated with a cell subset of interest in a test sample comprising a mixed cell population containing that subset of interest. A test sample comprising the cell subset of interest is labelled, such that substantially all cells of the subset of interest are uniformly labelled with a detectable reporter substance so that they can be enumerated. Each of two aliquots is then contacted with a receptor-selective marker which is binds specifically to the pre-determined lipoprotein receptors, thereby rendering those receptors detectable. The first aliquot of the test sample is maintained under conditions which substantially inhibit metabolic activity of the pre-determined lipoprotein receptors associated with the cell subset of interest. The second aliquot of the test sample is maintained under conditions which substantially optimize the metabolic activity of those lipoprotein receptors. Each aliquot is then contacted with a specific binding substance which binds specifically to at least one characteristic determinant of the cell subset of interest, thus forming a complex between the cell subset of interest and the specific binding substance. The complex is then separated from the other components of each aliquot, and the relative number of receptors per cell in each aliquot is determined by: (1) detecting the amount of detectable reporter substance, (2) detecting the amount of receptor-selective marker, and (3) determining the ratio of receptor-selective marker to detectable reporter substance. In a preferred embodiment, the detectable reporter substance is separated from the cells in the separated complex before the measurement of the detectable reporter substance is made.

The metabolic capacity of the lipoprotein receptors is then assessed by establishing a ratio of the relative number of lipoprotein receptors per cell in the aliquot maintained under non-metabolic conditions to the aliquot maintained under optimal metabolic conditions.

According to another aspect of the invention, a method is provided for determining the presence of abnormalities in the apoprotein component of a lipoprotein in a test sample. In particular, the method is applicable to abnormalities affecting the ability of the lipoprotein to interact normally with its cognate lipoprotein receptor. According to this method, there is provided a detectable lipoprotein binding reagent, which has binding sites that bind specifically to the apoprotein component of the lipoprotein. There is also provided a labelled lipoprotein standard which reproducibly binds to the lipoprotein binding reagent. The labelled lipoprotein standard may comprise a lipoprotein or the apoprotein of a lipoprotein. A test sample is obtained, which is suspected of having an abnormally binding lipoprotein (due to an abnormality in the apoprotein component), and a dilution series of assay samples is prepared. Each assay sample comprises, in a fixed total volume, (1) a fixed amount of the lipoprotein binding reagent, (2) a fixed amount of the labelled lipoprotein standard and (3) a fixed volume of the test sample or a dilution thereof. The fixed amount of labelled lipoprotein standard, combined with the lipoprotein present in the test sample, should slightly exceed the approximate amount needed to occupy all of the binding sites of the lipoprotein binding reagent.

The assay samples are incubated under conditions suitable to permit binding of the labelled lipoprotein standard and lipoprotein present in the test sample to the lipoprotein binding reagent. The basis of the assay is competition between the labelled apolipoprotein standard and the lipoprotein of the test sample. If the patient's lipoprotein are capable of binding normally to binding sites on the lipoprotein binding reagent, they will be able to compete better with the labelled lipoprotein standard for binding sites. If the patient has impaired lipoprotein binding capability, his lipoprotein will be less able to compete for binding sites on the lipoprotein binding reagent.

Each assay sample is then contacted with a specific binding substance capable of binding specifically to a characteristic determinant of the lipoprotein binding reagent, under conditions causing binding of the specific substance to the lipoprotein binding reagent. Thus, a complex between the specific binding substance and the lipoprotein binding reagent is formed, and the complex can be separated from other components in each assay sample.

The amount of lipoprotein binding reagent in each assay sample is quantitated by measuring the detectable label incorporated therein. The amount of labelled lipoprotein standard associated with the lipoprotein binding reagent in each assay sample is also measured, and the relative amount of labelled lipoprotein standard per fixed amount of lipoprotein binding reagent is determined. This ratio represents the fraction of those binding sites occupied by the labelled apolipoprotein standard in each assay sample, and is inversely proportional to the fraction of binding sites occupied by the patient's lipoprotein in the test sample. Thus, the ability of the lipoprotein in the test sample to bind to its cognate lipoprotein receptor may be assessed. This assessment is further facilitated by comparing a test sample from a patient suspected of having lipoprotein with abnormal binding capabilities to a test sample from an individual known to have lipoprotein of normal binding capabilities.

According to yet another aspect of the present invention, a method is provided for making a receptor-selective marker, which may be used advantageously in the practice of the present invention. The receptor-selective marker comprises a lipoprotein particle and a stably-associated detectable moiety, and is capable of binding specifically to a predetermined lipoprotein receptor, thereby detectably labelling that receptor. The preparative method involves providing, e.g., by isolation and purification from a natural source, lipoprotein particles that bind selectively to the predetermined lipoprotein receptor. After purification, such particles are suspended in a buffer comprising a fairly high concentration of a salt (e.g., 150 mM NaCl). The lipoprotein particles are then transferred to a labelling diluent which is capable of maintaining the functionality of the lipoprotein particles, while optimizing the stable association of the detectable moiety with the lipoprotein particles. The detectable moiety is chosen for its ability to become stably associated with the lipoprotein particles. According to a preferred embodiment, the labelling diluent consists essentially of a biologically compatible non-ionic buffer capable of regulating the osmolarity of the diluent to between about 250–350 mOs. Following transfer into the labelling diluent, the lipoprotein particles are contacted with the detectable moiety, thereby forming a receptor-selective marker which comprises a lipoprotein particle and a stably associated detectable moiety.

According to further aspects of the present invention, test kits are provided for carrying out the assays of the invention. A kit is also provided for preparing a receptor-selective label, according to methods of the present invention.

The present invention eliminates the need for the subjectivity of flow cytometric analysis and reduces the requirement for high cost instrumentation, such as a flow cytometer, allowing the use of low cost instrumentation, such as fluorescence-based multiwell plate readers. These new assay methods also provide for simultaneous processing of multiple patient samples, which is a marked advantage, especially in high volume clinical laboratories, over the sequential processing inherent in flow cytometry.

DETAILED DESCRIPTION

The present invention provides methods for detecting several genetic mutations which result in functional impairment of various stages of lipoprotein metabolism. Although this description focuses on lipoprotein metabolism, it will be appreciated that many metabolic functions involving binding of substances to cell surface receptors, followed by internalization of the bound substance, may be examined using the methods of the invention.

In one aspect of the invention, methods are provided to identify individuals having genetic mutations which result in reduced expression of lipoprotein receptors on cell surfaces. Expression of lipoprotein receptors on cell surfaces is necessary for the binding of lipoprotein particles for clearance and metabolism. In another aspect of the invention, methods are provided to assess internalization of bound lipoprotein, which is also essential for lipoprotein clearance and metabolism. Still another aspect of the invention involves methods for identifying individuals having mutations in the lipoprotein which result in the impairment of binding of lipoprotein to their cognate receptors. Such an impairment of binding often results from a mutation affecting the protein structure of the apoprotein portion of the lipoprotein. In another aspect of the invention, methods for preparing detectably labelled lipoprotein are provided.

A. Reagents and Components for Practice of the Invention

The term "lipoprotein", as used herein, refers to particles such as High Density Lipoprotein (HDL), Low Density Lipoprotein (LDL), Chylomicrons (CM), Very Low Density Lipoprotein (VLDL) and Intermediate Density Lipoprotein (IDL). The role of these lipoprotein is to assist in the processing or transport of free cholesterol, cholesterol esters and triglycerides. They are generally composed of phospholipids and proteins, along with the cholesterol or triglyceride moieties. The protein moiety of a lipoprotein is referred to as an "apoprotein". The apoprotein of LDL is known as "ApoB".

"Lipoprotein receptor" as used herein refers to functional domains on various cell types, such as blood cells or liver cells, which interact and bind specifically with a lipoprotein particle, such as those enumerated above. A lipoprotein receptor that is specifically recognized for binding by a particular lipoprotein particle (e.g., LDL) is sometimes referred to herein as the "cognate receptor" of that lipoprotein particle. For purposes of the present invention, the term "lipoprotein receptor" also refers to artificially created molecules, such as antibodies, capable of specifically interacting with and binding the lipoprotein particles.

For purposes of the present invention, the term "cells" is also intended to include other bioparticles capable of being assayed by the method of the present invention, but not necessarily comprising viable cells. The cells or bioparticles of interest may be present in test samples or specimens of varying natural or synthetic origin, including biological fluids such as whole blood, serum, plasma, urine, cerebrospinal fluid, amniotic fluid, lavage fluids and tissue extracts. In a preferred embodiment, the test sample is whole blood.

The analysis of lipoprotein receptor status is performed on cell suspensions or populations including subpopulations and subsets expressing a characteristic determinant. The term "determinant" is used herein in its broad sense to denote an element that identifies or determines the nature of something. When used in reference to the methods of the invention, "determinant" means that portion of the cell involved in and responsible for selective binding to a specific binding substance or detectable reporter substance, the presence of which is required for selective binding to occur. In general, naturally-occurring determinants are used in the methods of the invention. In one embodiment, however, a sample may be treated with an antigenic substance capable of stably associating with surface membranes of a cell subset of interest, thereby creating an artificial determinant on the cell subset of interest.

The term "specific binding", as used herein, means binding of one moiety to another, to the substantial exclusion of other moieties. For example, an antibody that binds specifically to a cell surface determinant binds substantially exclusively to that determinant, and not to any substantial extent to other determinants on the cell surface.

Cell-associated determinants include, for example, components of the cell membrane, such as membrane-bound proteins or glycoproteins, including cell surface antigens (also referred to herein as epitopes) of either host cell or viral origin, histocompatibility antigens, or membrane receptors. One class of specific binding substances used to selectively interact with these determinants are antibodies capable of immunospecifically recognizing antigens. The term "antibody" as used herein includes monoclonal or polyclonal antibodies immunoglobulins and immunoreactive immunoglobulin fragments. Further examples of characteristic determinants and their specific binding substances are: receptor—hormone, receptor—ligand, agonist—antagonist, Fc receptor of IgG—Protein A, avidin—biotin, virus—receptor and lectin-receptor. These are sometimes referred to herein as "specific binding pairs".

The practice of the present invention involves the selection of a cell type on which the measurement for lipoprotein receptor expression can be carried out. Though, traditionally, lipoprotein receptor deficiencies have been conducted on skin fibroblasts or hepatocytes, these sources do not permit an easily obtainable sample for routine testing. In a preferred embodiment, whole blood is used as the sample. For the receptor number and function assay, two criteria are important: 1) to select the cells or subsets of cells which possess the greatest potential for binding the lipoprotein particle of interest while being present in high enough frequency to provide a strong signal to noise ratio and 2) to select the cell subset of interest with the greatest reproduciblity and potential for internalization or processing of the lipoprotein particles such that normal and abnormal receptor functioning will be easily distinguishable. In a preferred embodiment, lymphocytes, preferably the CD4 or CD3 subsets, are utilized to provide maximal performance with regard to both criteria. Monocyte or neutrophil subsets are not preferred in the practice of this invention since they possess scavenger receptors for lipoprotein particles. These scavenger receptors non-specifically bind lipoprotein particles and will not provide a clear indication of the patient's potential for normal lipoprotein processing.

In the practice of the invention, quantification of the number of lipoprotein receptors present on cells or bioparticles in a test sample is carried out in part using a receptor-selective marker. The term "receptor-selective marker" is defined as a substance capable of binding specifically to a pre-determined lipoprotein receptor and providing an intense signal of sufficient intensity that it can be used to quantitate the amount of said substance bound. The amount of receptor-selective marker bound relates directly to the number of pre-determined lipoprotein receptors present in the sample. The receptor-selective marker may contain, for example, a naturally-occurring lipoprotein particle, (e.g., LDL) or apoprotein (the protein constituent of a lipoprotein particle which confers specificity for a given receptor type). Alternatively, it may be a specific binding protein or peptide, or an organic molecule such as a monoclonal or polyclonal antibody that binds to a specific lipoprotein receptor domain. The signal-generating component of the receptor-selective marker (also referred to herein as the "detectable moiety") may comprise a molecule, macromolecule or ion bound to or partitioned with the receptor-selective portion of the substance, and being capable of being detected. Suitable molecules include fluorescent dyes, adsorbent dyes, radio-isotopes or molecules capable of reacting with a second reagent to produce a detectable signal, e.g., molecules with enzymatic activity which can convert a nondetectable substrate into a detectable product. A method for preparing labelled lipoprotein particles for use as receptor-selective markers is set forth in greater detail below.

In the practice of the present invention, the receptor-selective marker is reacted with a sample containing lipoprotein receptors under reagent-excess conditions, to allow complete saturation of all available lipoprotein receptor sites, after which any unbound substance is removed from the sample by washing.

To assay test samples in batch mode rather than single cell analysis mode, a second signal is required which can be used to quantitate the number of cells or particles containing the lipoprotein receptors to be analyzed. The use of this second signal ensures that any differences in the quantity of receptor-selective marker observed is due to an actual modification or alteration in lipoprotein receptor expression levels, rather than to a variation in the number of cells or particles being measured. This second signal, herein referred to as a "detectable reporter substance" should be a molecule, macromolecule or ion capable of directly generating a signal, or capable of reacting with a secondary component which is able to generate a signal. The signal-generating component of the detectable reporter substance may be detected by absorbance, fluorescence, radioactivity or enzymatic activity resulting in the formation of a detectable product. In a preferred embodiment, the detectable reporter substance should be detectable by the same means as the receptor-selective marker. The detectable reporter substance must be capable of uniformly labeling the cells of the test sample, or all cells of a given subset of interest in a mixed cell population, such that a linear relationship exists between the signal generated by the detectable reporter substance and the number of cells of interest in the sample.

The detectable reporter substance may uniformly label the cell subset of interest by coupling to a uniformly-expressed determinant on the surfaces of the cells, in such a way as to avoid interfering with subsequent binding steps of the invention. Coupling of the detectable reporter substance to cell surfaces may be achieved by a variety of methods. In a preferred embodiment, the detectable reporter substance is bound to an antibody which itself binds specifically to at least one uniformly-expressed determinant of the cells of interest. Monoclonal antibodies to particular cell surface determinants are used to great advantage in this embodiment. For example, lymphocytes, which comprise a subpopulation of whole blood and have a high expression of lipoprotein receptors, may be uniformly labelled with a reporter substance bound to a monoclonal antibody which is directed against a lymphocyte surface antigen (e.g., CD2, CD3, CD4, CD5).

In another embodiment, the detectable reporter substance is attached to one member of a specific binding pair (e.g., avidin), while the other member of the specific binding pair (e.g., biotin) is attached to a monoclonal antibody specific for a selected cell surface antigen. Coupling of the detectable reporter substance is accomplished by immunospecific binding of the antibody to the cell surface antigen, combined with binding of the members of the specific binding pair to one another. In a preferred embodiment, the attachment of the biotin to the antibody is made in such a way that the linkage may be cleaved under appropriate conditions, thereby liberating the detectable reporter substance from the cell subset of interest. Such linkage methods are known in the art.

As an alternative to surface coupling, another aspect of the invention involves uniform labelling whereby the detectable reporter substance enters and becomes internalized within cells. In a preferred embodiment, the detectable reporter substance comprises a compound capable of entering viable cells, undergoing hydrolysis by intracellular enzymes, the hydrolyzed product being capable of detection by means of fluorescence. The detectable hydrolyzed product remains within the cells during separation of subsets of interest, and can be measured upon extraction from separated complexes. A particularly useful compound for this embodiment is 2'7-bis(2-carboxyethyl)-5-(and-6) carboxyfluorescein, acetoxymethyl ester (BCECF-AM), which is hydrolyzed intracellularly to 2',7'-bis (carboxyethyl)-5-(and 6) carboxyfluorescein (BCECF). Other useful compounds include:

1-[2-amino-5-(6-carboxyindol-2-yl)-phenoxyl]-2-(2'-amino-5'-methylphenoxy)ethane-N,N,',N'-tetracetic acid, pentaacetoxymethylester;

3-acetoxy-5'(and 6')-acetoxymethoxycarbonyl-10-dimethylaminospiro[7H-benzo[c]xanthene-7,1'(3'H) -isobenzofuran]-3'-one;

fluorescein diacetate; and 5-(and-6)-carboxyfluorescein diacetate.

In another alternative, the detectable reporter substance may be uniformly incorporated into the cell population or subset of interest by becoming internalized within the cells and binding to some internal cellular component, such as nucleic acid. In a preferred embodiment, stains capable of binding to the DNA or RNA in the nucleus of the cell are utilized. For example, Hoescht nuclear stains may be used to advantage in the practice of the present invention.

In a preferred embodiment of the present invention, the detectable reporter substance and/or the receptor-selective marker, or the detectable portions thereof, are separated from the cell subset of interest prior to being quantitatively measured. This step is particularly important when fluorescent compounds comprise the detectable portions of said reporter substance and label, to increase the signal potential and minimize quenching that may occur due to enhanced label incorporation into the reporter substance. Separation of the detectable reporter substance and/or receptor-selective marker may be accomplished by many methods known in the art, e.g., by solubilization with a detergent, or partitioning of a non-polar compound into a suitable organic solvent.

A method for separating cells or cell subsets is also required for the practice of the invention to facilitate washing of the samples and to expedite sample processing time. A specific binding substance and a solid support are the reagents used for this purpose. The term "specific binding substance" as used herein is defined as a molecule or macromolecule which is capable of interacting selectively with a characteristic determinant of the cells, or subset of cells, present in the test sample. The specific binding substance may be a monoclonal or polyclonal antibody, for example, with reactivity toward a unique CD-antigen present on the cell surface (e.g., CD3 or CD5). Alternatively, the specific binding substance may comprise magnetic or paramagnetic particles capable of being ingested by a selected cell subset (e.g., iron particle phagocytosis by macrophages). Additionally, the specific binding substance may comprise macromolecules capable of being reacted with or inserted into the membrane of cells; such macromolecules artificially acting as unique antigens (e.g., compounds of Formula I, discussed hereinbelow). The specificity of the specific binding substance should be unique in that there should be no appreciable cross-reactivity or interference with binding or incorporation of the receptor-selective marker.

The solid support enables the cells of interest to be separated from the other cells in the sample. The term "solid support" as used herein refers to a particulate or solid matrix having characteristics which allow it, or a compound attached to it, to react with the specific binding substance. The solid support to which the specific binding substance is affixed should be easily separable from the cell sample. Alternatively, the solid support should be fixed such that the unbound constituents in the sample may be washed away from it. Examples of solid supports may be, but are not limited to, magnetic or paramagnetic plates, beads or particles, high density particles made of materials such as polystyrene or latex with high sedimentation coefficients, immobile supports such as porous isolation columns, nylon or nitrocellulose membranes or plastic immobile supports, such as polymer plates or dishes (e.g., 96-well ELISA plates).

In a particularly preferred embodiment of the invention, the specific binding substance is affixed to a magnetic solid phase, which may comprise ferromagnetic, paramagnetic or diamagnetic material, thereby forming complexes or aggregates with the cell subset of interest which are magnetically separable from the test medium. Suitable procedures for coupling specific binding substances to a magnetic solid phase, e.g., magnetite particles, are described in the literature. See, for example, E. Menz et al., Am. Biotech. Lab. (1986).

If the solid support itself is not capable of reacting with the specific binding substance, it will have attached to it a molecule or macromolecule which will be capable of reacting with the specific binding substance so that the specific binding substance becomes affixed to the solid support. Such a molecule or macromolecule is referred to herein as an "auxiliary specific binding substance". For example, a magnetic bead comprising a monoclonal antibody capable of reacting with the specific binding substance, may be utilized. If the specific binding substance comprises an antibody, for example, the solid phase may have affixed to it a second antibody directed toward a characteristic determinant of the first antibody. In one embodiment, the first antibody comprises a selected isotype and the second antibody binds specifically to a determinant of that isotype. In another embodiment, the first antibody comprises immunoglobulin obtained from a selected species and the second antibody binds specifically to a determinant of that immunoglobulin from that species. In another embodiment, the specific binding substance comprises an antibody chemically attached to biotin, and the solid phase is affixed with an auxiliary binding substance comprising avidin. In this embodiment, the biotin may be attached to the antibody by a cleavable linkage, thereby enabling separation of the solid phase from the specifically bound cells of interest, if desired. In another embodiment, the solid support is affixed with a chemical reactive group, e.g., a tosyl group, capable of reacting with a constituent group of the specific binding substance.

Any of the foregoing methods of the invention may utilize various standards to great advantage. Such standards may include, but are not limited to pre-determined amounts of: (1) a detectable reporter substance; (2) receptor-selective marker; (3) cell subsets of interest which have been uniformly labelled with detectable reporter substance; and (4) cell types bearing pre-determined receptors having known affinities for a selected lipoprotein. The use of such standards in assays of the type described herein is common practice in the art.

The methods of the invention may be performed using conventional containers, including test tubes, multiwell plates, and the like. Detectors for accurately measuring the level of reporter substances in a test sample, such as a calorimeter, a spectrophotometer, a fluorospectrophotometer, a reflectometer, a liquid scintillation counter or a gamma counter, are commercially available.

According to another aspect of the invention, premeasured quantities of the different reagents, together with the various accessories used in practicing the methods of the invention, including diluents, cleaving agents, solid supports, one or more standards, or instructions for the preparation thereof may be conveniently packaged in a test kit. The reagents included in the test kit may take various forms. The receptor-selective label and detectable reporter substance may be provided in the form of solutions, together with suitable diluents. The solutions may be provided in containers suitable for performing the methods of the invention. Alternatively, the reporter substances and other reagents may be packaged dry, together with separate vials of diluent or solvent for addition to the reagents in the course of carrying out the methods. The specific binding substance is preferably provided immobilized on a solid support, which may be suspended in a suitable buffer, lyophilized or dried.

B. Competitive Assay for Determining Apoprotein Binding Affinity

According to another aspect of the present invention, a method is provided for evaluating the ability of a patient's lipoprotein particles to bind to their cognate lipoprotein receptors. Mutations in the structure of the apoprotein portion of the lipoprotein particle can affect this binding ability, resulting in the impairment of lipoprotein metabolism. The basis for the presently claimed assay is competition between a patient's lipoprotein and a labelled lipoprotein standard (or other receptor-selective marker, as described herein), of known binding capabilities, for binding to a known quantity of a lipoprotein binding reagent. The lipoprotein binding reagent may be a cell line with a high expression of the lipoprotein receptor of interest, which can be grown easily in culture to provide a continual source of the reagent. Such cells may be used fresh or they may be preserved in some manner, such that the receptor-lipoprotein binding interaction is maintained. Alternatively, a synthetic lipoprotein binding reagent may be created and employed, an example of which may be a magnetic or latex bead with monoclonal or polyclonal antibodies directed toward the apoprotein of the lipoprotein particle of interest, or a receptor specific for the particle of interest. If a cell line is utilized as the lipoprotein binding reagent, the basic requirement for selection of such a cell line is that it comprises a characteristic determinant by which cells can be enumerated, a characteristic determinant which can be utilized to bind a specific binding substance for cell separation and receptors for the lipoprotein particle of interest.

The assay is conducted by preparing various assay samples containing the lipoprotein binding reagent (which has been uniformly labeled with a detectable reporter substance), a fixed amount of labelled lipoprotein standard and a fixed volume of various dilutions of the lipoprotein of interest from the patient. The patient's lipoprotein is preferably provided as a sample of blood serum. An excess of labelled lipoprotein standard, alone or in combination with the patient's lipoprotein contained in the assay sample, must be used to ensure complete saturation of all the lipoprotein receptors present in the sample. Also, a concentration balance between the labelled lipoprotein standard and the patient's lipoprotein should be maintained, so as to allow for good resolution and signal detection through equilibrium binding. The sample is allowed to incubate, e.g., for at least 2 hours at room temperature to permit equilibrium binding of the labelled lipoprotein standard and of the patient's lipoprotein particles.

After the incubation, the samples are reacted with a specific binding substance affixed to a solid support, thereby separating the lipoprotein binding reagent, and lipoprotein bound thereto, from the assay samples. The lipoprotein binding reagent is enumerated by measuring the amount of detectable reporter substance incorporated therein. The labelled lipoprotein standard is then measured for each assay sample. Results for each sample are expressed as a ratio of the amount of labelled lipoprotein standard to the amount of detectable reporter substance measurement. The ability of a patient's lipoprotein to bind the lipoprotein binding reagent is assessed by comparing the above-described competition assay with a standard competition assay, e.g., using serum having normally-binding lipoprotein.

In a preferred embodiment, a negative control may also be included in the above-described lipoprotein binding assay. A negative control comprises a labelled lipoprotein that reproducibly binds to the lipoprotein binding reagent with a binding affinity approximately the same as that of an abnormal lipoprotein. For example, lipoprotein from serum of non-human species have been found to possess differential binding affinities for a lipoprotein binding reagent designed to bind human lipoprotein. Because these binding affinities are generally reproducible, non-human serum may be used to measure the degree of abnormality of the human lipoprotein being tested. Methods for performing the competitive lipoprotein binding assay are set forth in greater detail in Example 3 below.

C. Preparation of Labelled Lipoprotein Particles to be Used as a Receptor-Selective Marker or Labelled Lipoprotein Standard As defined previously, the receptor-selective marker is used in the method of the invention to evaluate the expression and/or metabolism of lipoprotein receptors in cells or various subsets of cells. It is also used as a labelled standard to evaluate the binding capability of a patient's lipoprotein to a lipoprotein binding reagent. Another aspect of the present invention relates to a method of preparing labelled lipoprotein particles which can serve as the receptor-selective marker or standard in these assay systems. Lipoprotein particles of interest are isolated using standard isolation techniques such as density centrifugation, ultra centrifugation or tangential flow methods, according to methods known in the art. See, e.g., Harel et al., J. Clin. Invest., 34: 1345–53 (1955); Pritchard et al., Anal. Biochem., 174: 121–22 (1988). Purified lipoprotein particles are then dialyzed against a suitable buffer solution and carried through the labelling process. The labelling process involves the transfer of the lipoprotein particles from traditional dialysis buffers, such as 0.15 M NaCl+0.3 mM EDTA+5 mM HEPES-KOH (pH 7.5) to a suitable diluent which can be used for labelling with a detectable moiety. See Table 1 infra.

For fluorescence labelling, the lipoprotein particles can be rendered fluorescent by the incorporation of a highly aliphatic or lipid soluble fluorochrome into the lipoprotein particles. Examples of such fluorochromes include, but are not limited to, compounds such as 1,1'-dioctadecyl-3,3,3', 3'-tetramethylindocarbocyanine perchlorate (DiI), 3,3'- dioctadecyloxacarbocyanine perchlorate (DiO), 3,3'-ditetradecylthiacarbocyanine (DiS), and Acridine long chain dyes. In a preferred embodiment, a membrane-binding compound of formula I shown below is used:

$$R—B—R_1 \quad \text{I}$$

wherein B represents a detectable substance and R and $R_1$ represent substituents independently selected from the group of hydrogen, alkyl, alkenyl, alkynyl, alkaryl or aralkyl, the hydrocarbon chains of which are linear or branched, said substituents being unsubstituted or substituted with one or more non-polar functional groups, one of R or $R_1$ having at least 12 linear carbon atoms and the sum of the linear carbon atoms in R and $R_1$ totaling at least 23.

Compounds of this formula bind stably to cell surface membranes, or bio-particles having lipid bilayer membranes. A method for preparing a receptor-selective marker comprising a compound of formula I above is set forth in Example 1, below.

Compounds of formula I above preferably comprise a chromophore as the detectable moiety (B). In other preferred embodiments, the detectable moiety comprises a radioactive molecule or a chelating moiety designed to chelate a radio-isotopic rare earth metal. In another embodiment, the detectable moiety may comprise a substance that reacts with a second substance to generate a detectable signal, e.g., biotin, which may be reacted with avidin bound to an enzymatic compound capable of generating a detectable product.

In a preferred embodiment, B represents a compound of the formula:

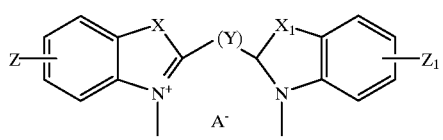

wherein
X and $X_1$ may be the same or different and represent O, S, $C(CH_3)_2$ or Se;
Y represents a linking group selected from $=CR_3—$, $=CR_3—CR_3=CR_3—$, $=CR_3—CR_3=CR_3—CR_3=CR_3—$, or $=CR_3—CR_3=CR_3—CR_3=CR_3—CR_3=CR_3—$, wherein $R_3$ is selected from H, $CH_3$, $CH_2CH_3$, $CH_2CH_2CH_3$ or $CH(CH_3)_2$;
Z and $Z_1$ may be the same or different and represent substituents selected from the group H, alkyl, OH, —O-alkyl, CON-$(alkyl)_2$, NH-acyl, NH-alkyl, N$(alkyl)_2$, $NO_2$, halogen, Si$(alkyl)_3$, O-Si$(alkyl)_3$, Sn$(alkyl)_3$ or Hg-halogen, the alkyl groups comprising Z and $Z_1$ substituents having from 1 to 4 carbon atoms; and A represents an anion. Compounds of Formula I and II above are commercially available (Zynaxis Cell Science, Inc., Malvern, Pa.). In particularly preferred embodiments, B represents oxacarbocyanine or indocarbocyanine.

Using any of the detectable moieties described above, the following methodology may be employed to incorporate such molecules into the lipoprotein particles of interest. Incorporation of large amounts of signals per lipoprotein particle will require that the detectable moiety have high solubility characteristics in a diluent capable of maintaining the integrity and affinity of the lipoprotein particles. Salt-based isotonic diluents with osmolarity conditions suitable for lipoprotein particles are not optimal for practice of the labelling method, since they do not permit maintenance of the detectable moiety in monomeric form. Instead, they foster micelle formation, which retards or minimizes incorporation of the detectable moieties into the lipoprotein particles. Other organic diluent solutions, such as heptane, have been employed. However, these often provide a more soluble environment for the detectable moiety than for the lipoprotein particle, thus discouraging selective partitioning of the detectable moiety with the lipoprotein particle. The use of organic diluents such as heptane also commonly involve lyophilization of the lipoprotein sample prior to dissolving lipoprotein in the organic solutions, due to water and organic solution immiscibility. The present invention employs labelling diluents that maintain lipoprotein structure and function, reduce handling and manipulation and allow for a preferential partitioning of the detectable moiety with the lipoprotein particle. Diluents which may be employed successfully include osmolarity-regulating solutions (250–350 mOs) of the following compounds, either singly or in combination:

TABLE 1

| Osmolarity Regulating Agent | Relative Fluorescence Intensity (CONC) | |
|---|---|---|
| | DiS-$C_{14}$-(5) | DiO-$C_{14}$-(3) |
| Ethanol | 100 | 100 |
| Glucose | 31 | 100 |
| Fructose | 35 | 100 |
| Sorbose | 40 | 100 |
| Sucrose | 41 | 100 |
| Xylose | 36 | 19–52 |
| Ribose | 24 | 100 |
| Lyxose | 0.12 | 1.8 |
| Glycine | 31 | 93 |
| Arginine | 17 | 17.2 |
| Glycerol | 39 | 99.5 |
| Inositol | 42 | 92 |
| Xylitol | 34 | 76.4 |
| Mannitol | 29 | * |
| Adonitol | 34 | ND |
| Tris(hydroxymethyl)-methylaminopropane sulfonic acid (TAPS) | 18 | ND |
| 3-(Cyclohexylamino)-1-propanesulfonic acid (CAPS) | 40 | ND |
| N-(2-Hydroxyethyl)piperazine-N'-3-propane-sulfonic acid (EPPS) | 18 | ND |
| N-2-hydroxyethyipiperazine-N'-2-hydroxy-propane-sulfonic acid (HEPPSO) | 20 | ND |
| 3-[N-N-bis(-2-hydroxyethyl)amino]-2-hydroxypropanesulfonic acid (DIPSO) | 43*** | ND |
| NaCl | 6 | 1.7 |
| Phosphate Buffered Saline | 2.1 | 6.5 |
| $Na_2SO_4$ | 7.4 | 1.6 |
| NaI | 1.1 | 0.14 |
| Choline Chloride | 11** | 6.3 |
| Choline Iodide | 0.16 | 2.3 |

*Precipitate in ethanol, no data obtainable
**Artifact due to large crystals did not pellet
***Precipitate in ethanol.
ND Not determined While the above list fulfills criteria for maintaining lipoprotein structure and permits selective partitioning of the detectable moiety into the lipoprotein, another factor must be taken into consideration in the practice of the present invention. Lipoproteins may exist in the native non-oxidized form, or they may become oxidized over time under certain conditions. To accurately enumerate selected lipoprotein receptors, non-oxidized lipoprotein should be used to eliminate or minimize general non-specific lipoprotein binding, and interference by scavenger receptors, which will also non-selectively bind the oxidized form of the lipoprotein. Of the complete list of compounds which will provide the desired conditions for partitioning of signal compounds into lipoprotein particles, several promote oxidation while others have been found to minimize it.

TABLE 2

Lipoprotein Oxidation in Various Diluents

| LDL SAMPLE DILUENT EMPLOYED | UNTREATED SAMPLE | BHT TREATED CONTROL |
|---|---|---|
| CHES (Good's Buffer) | 1.591 | 1.036 |
| Glycine | 1.026 | 1.001 |
| Fructose | 1.218 | 1.126 |
| Sucrose | 1.146 | 1.003 |
| Xylitol | 1.061 | 1.046 |
| Glucose | 1.479 | 1.141 |

Table 2 presents measurement of lipoprotein oxidation, utilizing a fluorescence measurement at an excitation wavelength of 360 nm and an emission wavelength of 430 nm, which differentiates oxidized versus non-oxidized LDLs. Non-oxidized controls comprise butylated hydroxytoluene (BHT) added to the lipoprotein solution as an antioxidant. As illustrated in Table 2, although glucose may in fact provide good labelling of lipoprotein particles (Table 1), it also promotes the oxidation of the particle. In contrast, glycine also provides good incorporation of a detectable moiety into the lipoprotein, but oxidation does not occur to any significant degree. Thus, for the method of the present invention, glycine is preferred as a osmolarity-regulating solution for labelling lipoprotein particles. A protocol for labelling low density lipoprotein with a compound of formula I above is set forth in Example 1 below.

Examples 1–3 below illustrate use of the methods and reagents of the present invention for identifying patients as either normal or abnormal with regard to lipoprotein receptor expression, receptor functioning and affinity of the apo-B protein of LDL particles for its cognate lipoprotein receptor. These examples are intended to illustrate and not to limit the invention.

EXAMPLE 1

LABELLING LOW DENSITY LIPOPROTEIN (LDL) WITH A FLUORESCENT MEMBRANE-BINDING COMPOUND OF FORMULA I

A. Lipoprotein Preparation

Freshly isolated (non-oxidized) LDL, not older than 2 weeks, is dialyzed in buffer for at least 48 hours prior to labelling. The buffer consists of 0.15 M NaCl, 0.3 mM EDTA, pH 7.5, supplemented with 5 mM HEPES. Dialysis is carried out at 4° C. under nitrogen if possible, or in buffer flushed with nitrogen. The LDL is then filter-sterilized (0.45 nM filter) to avoid bacterial contamination. The LDL is dialyzed at 4° C. for 48 hours (3 changes of the diluent), preferably under nitrogen, against a labelling diluent (isosmotic, salt free, non-oxidative) in order to remove salts. Glycine or xylitol are suitable diluents since they show the least oxidation potential for LDLs (see Table 2, supra). Even slight salt contamination should be avoided. LDL should be handled under sterile conditions, and antioxidants should be chosen carefully. During isolation of the LDL from the blood, 20 nM BHT, 0.03 mM EDTA, 200 U/L vitamin E, 0.1% reduced glutathione can be used as a mixture for best results, however each component may be used individually. During dialysis however, BHT and vitamin E should be used very carefully if at all, since they can be incorporated into the LDL particle and decrease dye incorporation and affinity to the LDL receptors.

B. Labelling Mixture

A fluorescent membrane-binding compound (hereinafter FMBC) of formula I above is used for labelling isolated LDL. For example, PKH 26-GL is supplied as a 1 mM solution in ethanol from Zynaxis Cell Science, Inc. (Malvern, Pa.). A 1:5 dilution is prepared using an optimal diluent (glycine) providing a 20 $\mu$M final solution. Glycine or xylitol is recommended to control oxidation, and serve as the diluents of choice. However, other diluents such as those listed in Table 1 with values >20 will support solubilization of the dye for delivery to the particle, but oxidation potential should be monitored. The amount of LDLs to be labelled will dictate the labelling conditions and column size necessary to isolate the labelled LDL particles from the free unbound dye. The following combinations have proven workable: (1) 2 mls LDL in diluent+2 mls 20 $\mu$M FMBC in diluent with use of a 32 cm by 3.5 cm column for isolation; 1 ml LDL in diluent+1 ml 20 $\mu$M FMBC in diluent with use of a 37 cm×1.5 cm column for isolation.

Labelling is carried out under the following conditions to label 2 mls of LDL preparation. The steps should be performed as rapidly as possible, in the exact order specified, and preparation of solutions should occur immediately prior to conducting the labelling reaction: Temperatures of 4° C. to 15° C. should be used for labelling.

Prepare the stock solution of FMBC at a 20 $\mu$M final concentration in diluent (glycine, pH 7.0, osmolarity of 280–300). Add 50 $\mu$l of DMSO (25 ul/100 ul FMBC) to enhance the fluorochrome-to-protein ratio for labelling. Addition of more DMSO will result in overlabelling and inactivation of the LDL particles. Immediately before the addition of LDLs, add 3 ml of 20% Bovine Serum Albumin (BSA; Fraction V) in diluent to the mixture (300 ul/200 ul) of FMBC labelling solution). Fraction V BSA is fatty acid free and has low proteolytic activity, so it serves to protect the LDL particles. The BSA must be added immediately prior to the addition of LDLs, to prevent BSA/dye association. The final concentration may range from 4–10%. A final concentration of less than 4% BSA will result in some denaturation of the LDL particles, while a final concentration of greater than 10% will create difficulties in separation of the LDL particles on the column. The addition of BSA compares well with other labelling methods using serum or starch method, and provides advantages in the final purification steps not found in the serum or starch methods. Immediately add the LDLs in diluent. Proper concentrations are from 1.5 to 3 mg LDL/ml per 100 ul of 1 mM FMBC. The addition of too much LDLs will result in a poor dye/LDL ratio whereas too little will dilute the final product and presents the potential for overlabelling. The recommended labelling time is 15 minutes, not to exceed 30 minutes (prolonged exposure could denature LDL).

C. LDL Separation From the Labelling Mixture

Separation of labelled LDL from the labelling mixture can best be accomplished by gel filtration in Sephacryl S-300 or S-1000 (Pharmacia). Separation may also be accomplished by ultra-centrifugation, however the process requires 3–4 days and may increase the oxidation rate.

The column size should be appropriate to the volume of the labelling mixture. The column should be equilibrated and run with a buffer comprising 0.12 M NaCl, 10 mM Tris-HCl (pH 7.5), 0.3 mM EDTA, 0.01% NaN$_3$.

Fractions are collected and analyzed as soon as possible; fraction size depends upon column size (1 or 2 ml). Protein concentration can be assessed by measuring absorbance at 280 nm and FMBC concentration at the peak emission wavelength of FMBC (provided with suppliers' instructions, e.g., for PKH 26-GL, 500 nm). Cholesterol level can be measured with Sigma Kit No. 352 (optional).

The best two or three fractions are pooled and centrifuged for 30 minutes at 4° C., 3000×g and filtered with a 0.45 nM filter. Store in a small, tightly closed container under Nitrogen at 4° C. in the dark. Anti-oxidants may also be added for longer term storage.

The separation procedure should be performed at 4°–15° C., preferably in the dark. Fluorescence intensity per microgram of the protein is measured using a Lab Systems fluoroscan (3,3 setting) and the oxidation level is assessed by measuring fluorescence (1,1 setting) or by Iodine oxidation testing.

Several studies were completed to assess the performance characteristics of material from commercial sources compared with the material produced from the methods of this invention. The results are set forth in Table 3.

TABLE 3

Comparison of LDL Prepared by the Method of the Invention with Other Commercial Sources

| SAMPLE | DYE/LDL RATIO (1) | OXIDATION MEASUREMENT (2) | | CELL BINDING (3) | |
| --- | --- | --- | --- | --- | --- |
| | | Value | % oxid. | 4° C. | 37° C. |
| CS #1-1 HUMAN | 20 | 1.8 | 23% | 2.93 | 8.27 |
| CS #1-2 HUMAN | 25 | 1.5 | 12% | 6.3 | 16.42 |
| CS #2 HUMAN | 15 | 2.1 | 33% | 4.9 | 6.4 |
| ZYN #1 PORCINE | 30 | .97 | 0% | 5.6 | 18.87 |
| ZYN #2 PORCINE | 30 | 1.14 | 6% | 7.3 | 22.87 |
| ZYN #3 PORCINE | 30 | 1.09 | 4% | 6.75 | 18.85 |
| HUMAN CONTROL | 0 | | | | |
| UNOXIDIZED | | 1.15 | | | |
| OXIDIZED | | 4.0 | | | |
| PORCINE CONTROL | 0 | | | | |
| UNOXIDIZED | | .98 | | | |
| OXIDIZED | | 3.5 | | | |

(1) Dye/LDL ratio refers to the number of dye molecules incorporated into an LDL particle
(2) Oxidation measurement refers to the measurement of the samples at an absorbance of 360 nm which differentiates the oxidized versus non-oxidized state of the LDL particle. Low values are perceived as non-oxidized (see control samples), whereas high values indicate oxidation has occurred.
% Oxidized = [(sample value − control value unoxidized)]/(control oxidized − control unoxidized) * 100
(3) Cell binding values indicate the fluorescence signal obtained from incubating $10^5$ lymphoblast cells (GMO) with 100 ul of a 100 ug/ml solution of labeled LDL particles. The 4° C. values represent surface receptor binding while the 37° C. samples indicate values for surface and internalized receptor binding.
CS = commercial source
ZYN = prepared by method of invention using Zynaxis PKH-26-GL

EXAMPLE 2

LIPOPROTEIN RECEPTOR NUMBER AND FUNCTION ASSAY

The lipoprotein receptor number and function assay is performed on a blood sample as follows.

A blood sample is obtained from the patient using acid citrate dextrose anticoagulant to prevent clotting. The sample is derepressed to provide for maximal receptor expression. Derepression comprises removing the plasma component by centrifuging the sample, washing the cellular component (in e.g., Hanks Balanced Salt Solution (HBSS)-Ca-Mg, 0.25% BSA, 0.1% EDTA, 10 mM HEPES-KOH, pH 7.4) to remove residual plasma components (e.g. lipoprotein), and incubating the cells at 37° C. for 12–24 hours in lipid free medium to permit processing of any lipoprotein which may be bound to the cells. The media composition is important, and EDTA is included to dissociate any serum LDLs from the cells and to enhance receptor expression on cell surfaces. AIM-5 media (Gibco) has proven optimal for derepression. The result is a cell sample which has recycled lipoprotein-bound receptors and internal receptor pools to the cell exterior, maximizing potential for signal. After the incubation, the cells are centrifuged and resuspended in a volume of medium to the desired number of cells/ml.

LDL particles labelled with FMBC, according to the methods set forth in Example 1, are used as the receptor-selective marker to provide a red fluorescent signal to quantitate LDL receptor numbers. An excess of FMBC-labelled LDLs must be used to insure complete saturation of LDL receptors. This generally can be accomplished by using 100 ug of LDLs and $5 \times 10^6$ or fewer white blood cells. The LDLs are incubated with the concentrated blood sample for 2 hours at 4° C. to permit binding but no internalization of the LDL particles (i.e., a metabolically inhibitory temperature). A second set of samples are identically prepared and incubated at 37° C. for two hours to permit the internalization process to take place. An unlabelled control sample is also prepared to account for background signals.

After the LDL incubation, the cell samples are all cooled to 4° C. and are reacted for 30 minutes at 4° C. with a detectable reporter substance and a specific binding substance affixed to a solid support. These conditions are used for both the 4° C. and 37° C. LDL incubation samples. In this example, beta-galactosidase-conjugated antibody directed against the CD2 surface antigen of lymphocytes is used as the detectable reporter substance, at a concentration of 2–5 ug of antibody per 100 ul of whole blood (or $10^6$ cells). The CD2 antigen is uniformly expressed on the cells of interest and will provide a linear relationship by which cell number can be determined. The specific binding substance/solid support is a monoclonal antibody attached to a magnetic bead either directly or indirectly and is directed toward the CD3 antigen. This CD3 antigen is present but does not interfere with the LDL receptor or CD2 binding domains. The magnetic bead to cell ratio should be 2 or greater to provide for saturation of all CD3 antigens present on the cell surface and the binding reaction is carried out for at least 30 minutes (or the time required to achieve saturation binding, which can be determined empirically) at 4° C. to prevent capping or shedding of the bound antibody by the cell.

At the conclusion of the incubation, the cells are placed in a magnetic field which will separate the cells which have formed a complex with the magnetic particles. The sample is washed several times using Hanks Balanced Salt Solution (HBSS)+Ca+Mg, 1% BSA in 10 mM HEPES-KOH (pH 7.6) to remove unbound LDL particles and any unbound or unincorporated reporter substances. The sample is then reacted with a substrate solution (e.g., methylumbelliferone) at a concentration of 0.1–1.0 mM (preferably 0.6 mM) to develop the signal component of the detectable reporter substance. This reaction is carried out at 30° C. for 30 minutes.

At the conclusion of the incubation, 50 ul of stop buffer containing 1% Triton X-100, 1 M glycine and 300 mM EDTA (pH 10) in water is added to the samples. The Triton serves to solubilize the cells and LDL particles, thereby releasing the FMBC component of the receptor-selective marker and enhancing its quantum efficiency.

The samples are then analyzed using a fluorescence based plate reader. The FMBC is measured using optimum excitation and emission wavelengths, according to the specifications provided by the supplier (e.g., for PKH 26-GL, 544 nm excitation wavelength and 590 nm emission wavelength). The filters are then changed in the instrument and the samples are measured again using optimum excitation and emission wavelengths (e.g., 355 nm and 420 nm, respectively) to detect the signal from the detectable reporter substance and determine cell number. Results are expressed as a ratio of FMBC signal to detectable reporter substance signal to provide information as to the number of receptors per cell for both the 4° C. receptor binding samples and the 37° C. internalization samples.

EXAMPLE 3

LDL/Apo B BINDING ASSAY

Evaluation of the binding capability ApoB proteins of LDL particles is performed as follows.

A blood sample is obtained from a patient using a red top Vacutainer® to promote clotting of the sample. The serum is collected from the tube and used for the diagnostic test. A LDL binding reagent is used as a source of receptors for the lipoprotein of interest. This example employs a cultured cell line, of human acute lymphoblastic leukemia cells (CEM cells, ATCC, Rockville, Md.), as the lipoprotein binding reagent.

LDL particles labelled with FMBC according to the methods set forth in Example 1 are used as a labelled lipoprotein standard, providing a red fluorescent signal to quantitate the total number of receptors present in the sample, optimally consisting of $1 \times 10^4$ to $1 \times 10^6$ cells. The assay will provide information as to how well the LDLs from the patient's sample are able to compete with the labelled LDLs for receptor binding sites on the cells. This is accomplished by preparing various assay samples containing the lipoprotein binding reagent (i.e., the above-referenced CEM cells), a fixed amount of FMBC-labelled LDLs and a fixed volume of the patient's serum, e.g., $4 \times 10^5$ cells in 100 ul of binding buffer (HBSS+Ca+4mM Ca++, 2% BSA, 0.1% $NaN_3$), or various dilutions thereof. For example, 50 ul of FMBC-labelled lipoprotein at a concentration of 50 ug/ml and 100 ul of a 1:2, 1:4, 1:8, 1:16 diluted serum sample may be utilized. An excess of LDL particles (consisting of FMBC-labelled LDLs+unlabelled patient LDLs) must be used to insure equilibrium saturation of all of the LDL receptors present in the sample. The assay samples are allowed to incubate for at least 2 hours at room temperature to permit binding of the LDL particles. If fixed cell reagents are used, internalization will not occur.

After the LDL incubation, the assay samples are cooled to 4° C. and are reacted with the specific binding substance/solid support compound for 10–30 minutes at 4° C.

In this example, Hoechst nuclear stains are used as the detectable reporter substance. This compound fluoresces in the ultraviolet region and binds to the DNA in the cell nucleus. The concentrations used, ranging from 0.5 to 4.0 mg/ml are selected to provide a linear relationship between cell number and signal. The specific binding substance/solid support in this example is a monoclonal antibody attached to a magnetic bead either directly or indirectly and is directed toward the CD 5 antigen present on the CEM cells. This CD 5 antigen is present but does not interfere with the LDL receptor or DNA binding domains. The bead to cell ratio should be 2 or greater to provide for saturation of all CD5 binding sites present on the cell surface. The labelling is carried out for 30 minutes (or the time required to achieve saturation binding) at room temperature. If live cells are used as the LDL binding reagent, the bead incubation should be carried out at 4° C. to prevent capping or shedding of the antibody/bead complex by the cell.

At the conclusion of the incubation, the assay samples are placed in a magnetic field which separates the magnetic particles and attached cells. The cells are washed (HBSS+Ca+Mg+0.5% BSA, 0.02% $NaN_3$) to remove unbound LDL particles.

After washing, the samples are analyzed using a fluorescence based plate reader. The samples are measured using an excitation wavelength of 355 nm and an emission wavelength of 460 nm to detect the ultraviolet signal from the Hoescht nuclear stain to determine cell number. Next, 50 ul of 0.5% Triton X- 100 in 1 M glycine, pH 10, with 0.14 mM $NaN_3$ (final Triton concentration 0.1%) is added to the samples. The Triton serves to solubilize the cells and LDL particles, thereby releasing the FMBC component of the receptor-selective label and enhancing its quantum efficiency. The filters are then changed in the instrument. FMBC is detected using optimum excitation wavelengths (e.g., 544 nm and 590 nm, respectively, for PKH 26-GL) to provide a comparison of the samples containing FMBC labelled LDLs only (providing the maximum signal per sample value) and the samples containing FMBC labelled LDLs and dilutions of the patient's serum. Results are expressed as a ratio of FMBC signal to UV signal.

While certain preferred embodiments of the present invention have been described and specifically exemplified above, it is not intended to limit the invention to such embodiments. Various modifications may be made thereto without departing from the scope and spirit of the present invention, as set forth in the following claims.

What is claimed is:

1. A method of making a lipoprotein receptor-selective marker that comprises a lipoprotein particle and a stably-associated detectable moiety, said receptor-selective marker being capable of binding specifically to a lipoprotein receptor, thereby detectably labeling said receptor, said method comprising the steps of:
   a) providing lipoprotein particles that bind specifically to said lipoprotein receptor, said particles being suspended In an isotonic buffer comprising a salt;
   b) transferring said lipoprotein particles to an osmolarity regulating non-ionic labeling diluent capable of minimizing oxidation of said lipoprotein particles; and
   c) contacting said lipoprotein particles with a detectable moiety, thereby forming a receptor-selective marker that comprises a lipoprotein article and a stably-associated detectable moiety.

2. A method according to claim 1, wherein said labeling diluent comprises a biologically compatible non-ionic buffer capable of regulating the osmolarity of said diluent to between about 250–350 milliosmolar.

3. A method according to claim 2, wherein said nonionic buffer is selected from the group consisting of glycine and xylitol.

4. A method according to claim 1, wherein said labeling diluent comprises a reducing agent.

5. A method according to claim 1, wherein said detectable moiety is selected from the group consisting of:
1,1'-dioctadecyl-3,3,3',3'-tetramethylindocarbocyanine perchlorate (DiI);
3,3'-dioctadecyloxacarbocyanine perchlorate (DiO); and
3,3'-ditetradecylthiacarbacyanine.

6. A method according to claim 1, wherein said detectable moiety comprises a compound of the formula:

wherein B represents a detectable substance and R and $R_1$ represent substituents independently selected from the group of hydrogen, alkyl, alkenyl, alkynyl, alkaryl or aralkyl, the hydrocarbon chains of which are linear or branched, said substituents being unsubstituted or substituted with one or more non-polar functional groups, one of R or $R_1$ having at least 12 linear carbon atoms and the sum of the linear carbon atoms in R and $R_1$ totaling at least 23.

7. A method according to claim 6, wherein B represents a compound of the formula:

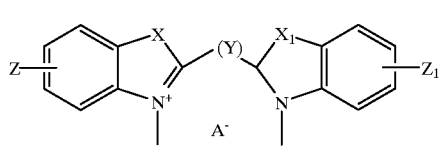

II wherein
X and $X_1$ may be the same or different and represent O, S, $C(CH_3)_2$ or Se;
Y represents a linking group selected from $=CR_3-$, $=CR_3-CR_3=CR_3-$, $=CR_3-CR_3=CR_3-CR_3=CR_3-$, or $=CR_3-CR_3=CR_3-CR_3=CR_3-CR_3=CR_3-$, wherein $R_3$ is selected from H, $CH_3$, $CH_2CH_3$, $CH_2CH_2CH_3$ or $CH(CH_3)_2$;
Z and $Z_1$ may be the same or different and represent substituents selected from the group H, alkyl, OH, —O-alkyl, CON-(alkyl)$_2$, NH-acyl, NH-alkyl, N(alkyl)$_2$, $NO_2$, halogen, Si(alkyl)$_3$, O-Si(alkyl)$_3$, Sn(alkyl)$_3$ or Hg-halogen, the alkyl groups comprising Z and $Z_1$ substituents having from 1 to 4 carbon atoms; and
A represents an anion.

8. A method according to claim 7, wherein B is selected from the group consisting of oxacarbocyanine and indocarbocyanine.

9. A test kit for determining the relative number per cell of at least one pre-determined lipoprotein receptor associated with a cell subset of interest in a test sample containing a mixed cell population, said subset of interest having at least one characteristic determinant, said test kit comprising a container which includes:

a) a detectable reporter substance for uniformly labeling cells of said subset of interest;

b) a lipoprotein receptor-selective marker for detectably labeling said pre-determined lipoprotein receptor; and c) a reagent comprising a specific binding substance affixed to a solid phase, said specific binding substance being capable of binding specifically to said at least one characteristic determinant of said cell subset of interest other than the predetermined lipoprotein receptor.

10. A test kit according to claim 1, which further includes at least one of:

a) a medium for uniformly labeling said cell subset of interest with said detectable reporter substance;

b) a medium for detectably labeling said predetermined receptors with said receptor-selective marker;

c) at least one predetermined standard for determining the number of cells in said cell subset of interest in said test sample;

d) reagents for detecting said detectable reporter substance and said receptor-selective marker.

11. A kit for preparing a receptor-selective marker comprising a lipoprotein particle and a stably-associated detectable moiety, said receptor-selective marker being capable of binding specifically to a predetermined lipoprotein receptor, thereby detectably labeling said receptor, said kit comprising:

a) a labeling mixture comprising said detectable moiety;

b) an osmolarity regulating non-ionic labeling diluent capable of minimizing oxidation of said lipoprotein particle; and c) a low density lipoprotein isolating solution for isolating and purifying said lipoprotein particle from whole blood.

12. A kit according to claim 11, further comprising a compartmentalized container, wherein said labeling mixture is provided in a first compartment of the container, said labeling diluent is provided in a second compartment of the container, and said isolating solution is provided in a third compartment of the container.

13. A kit according to claim 11, wherein said isolating solution contains 20 mM BHT, 0.03 mM EDTA, 200 U/L Vitamin E and 0.1% reduced glutathione.

14. A kit according to claim 11, further comprising an organic ionic buffer having a pH of about 7.2–8.0, said buffer being suitable for dialyzing purified lipoprotein particles.

15. A kit according to claim 14, wherein said buffer is provided in a fourth compartment of the container.

* * * * *